United States Patent
Ojima et al.

(10) Patent No.: US 9,845,296 B2
(45) Date of Patent: Dec. 19, 2017

(54) BENZIMIDAZOLES AND THEIR USE IN THE TREATMENT OF TUBERCULOSIS

(71) Applicant: The Research Foundation for The State University of New York, Albany, NY (US)

(72) Inventors: Iwao Ojima, Port Jefferson, NY (US); Divya Awasthi, Setauket, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/037,704

(22) PCT Filed: Nov. 19, 2014

(86) PCT No.: PCT/US2014/066286
§ 371 (c)(1),
(2) Date: May 19, 2016

(87) PCT Pub. No.: WO2015/077276
PCT Pub. Date: May 28, 2015

(65) Prior Publication Data
US 2016/0297769 A1 Oct. 13, 2016

Related U.S. Application Data

(60) Provisional application No. 61/907,610, filed on Nov. 22, 2013, provisional application No. 62/033,808, filed on Aug. 6, 2014.

(51) Int. Cl.
*A61K 31/415* (2006.01)
*C07D 235/00* (2006.01)
*C07D 235/08* (2006.01)
*A61K 31/4184* (2006.01)

(52) U.S. Cl.
CPC ........ *C07D 235/08* (2013.01); *A61K 31/4184* (2013.01)

(58) Field of Classification Search
CPC .......................... C07D 235/08; A61K 31/4184
USPC ........................................ 514/394; 548/304.4
See application file for complete search history.

(56) References Cited

U.S. PATENT DOCUMENTS 8,232,410 B2   7/2012   Ojima

FOREIGN PATENT DOCUMENTS

WO   WO2013142326 A1   9/2013

OTHER PUBLICATIONS

D. Awasthi et al., "SAR Studies on Trisubstituted Benzimidazoles as Inhibitors of Mtb FtsZ for the Development of Novel Antitubercular Agents", J. Med. Chem., vol. 56, No. 23, pp. 9756-9770 (Nov. 2013).
Kumar et al., "Novel Trisubstituted Benzimidazoles, Targeting Mtb FtsZ, as a New Class of Antirubercular Agents", J. Med Chem., vol. 54, pp. 374-381 (Feb. 2010).

*Primary Examiner* — Shengjun Wang
(74) *Attorney, Agent, or Firm* — Hoffmann & Baron, LLP

(57) ABSTRACT

The present invention relates to novel 2,5,6-benzimidazole derivatives and pharmaceutically acceptable salts thereof. Another aspect of the invention relates to methods of treating a patient infected by *Mycobacterium tuberculosis* by administering to the patient a 2,5,6-benzimidazole derivative or a pharmaceutically acceptable salt thereof.

2 Claims, No Drawings

BENZIMIDAZOLES AND THEIR USE IN THE TREATMENT OF TUBERCULOSIS

CROSS REFERENCE TO RELATED APPLICATIONS

This application claims priority to International Application No. PCT/US2014/066286 filed Nov. 19, 2014, which claims priority to U.S. Provisional Application No. 61/907,610, filed Nov. 22, 2013, and 62/033,808, filed Aug. 6, 2014, which are incorporated herein by reference.

This invention was made with government support under grant number AI078251 awarded by the National Institute of Health. The government has certain rights in the invention.

BACKGROUND OF THE INVENTION

Tuberculosis (TB) was one of the first infectious diseases to be identified. More than fifty years of research has been directed to controlling and eliminating this disease. However, the eradication of TB is still one of the most prominent challenges for basic and clinical research scientists.

Once thought to be under control, TB case reports in the U.S. increased sharply in the early 1990's. Although, this trend has reversed and the reported numbers of new cases has steadily declined in industrialized countries, TB remains a major global public health threat. Recent statistics from the WHO estimate that there are approximately 8.4 million new cases every year with a global mortality rate of 23% or approximately 2 million deaths per year.

Poor chemotherapeutics and inadequate local-control programs contribute to the inability to manage TB and lead to the emergence of drug resistant strains of the bacteria that cause *Mycobacterium tuberculosis* (Mtb). A survey conducted at 58 international sites between 1996 and 1999 found exceptionally high rates of single and multidrug-resistant strains in Estonia, Latvia and Russia, and revealed that countries such as China and Iran were developing a high prevalence of multidrug-resistance (MDR-TB). See Kruuner, A., Sillastu, H., Danilovitsh, M., Levina, K., Svenson, S. B., Kallenius, G., and Hoffner, S. E. (1998) *Drug resistant tuberculosis in Estonia, Int J Tuberc Lung Dis* 2, 130-3. Significantly, MDR-TB is much more difficult to treat than sensitive TB, requiring administration of more expensive, second-line antibiotics for up to two years. The frequency of resistance to at least one of the first-line TB drugs (isoniazid (INH), rifampicin (RIF), pyrazinamide or ethambutol) ranged from 1.7% in Uruguay to 36.9% in Estonia. The frequency of resistance is indicative of the global problem involving not only the spread of Mtb, but also treatment.

Finally, of critical importance is the role of TB as a major opportunistic pathogen in patients with HIV/AIDS. Consequently, there is a pressing need for the development of novel TB drugs that are effective against both sensitive and resistant Mtb strains.

New benzimidazole derivatives synthesized in the laboratory of Dr. Iwao Ojima were reported in U.S. Pat. No. 8,232,410 and PCT Application Nos. PCT/U52013/024601 and PCT/US2013/32083.

SUMMARY OF THE INVENTION

In one embodiment, the invention relates to a compound having the formula:

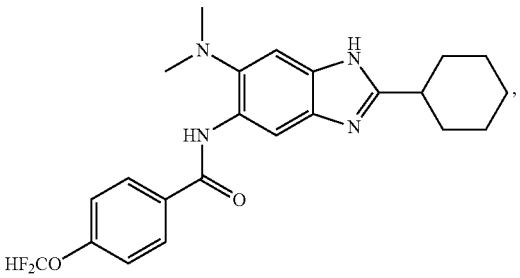

SB-P17G-A19

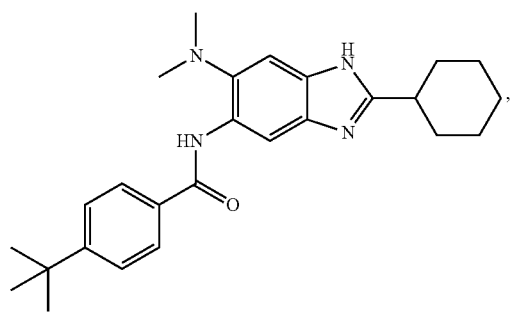 [SMILES: CN(C)c1cc2[nH]c(C3CCCCC3)nc2cc1NC(=O)c1ccc(C(C)(C)C)cc1]

SB-P17G-A23

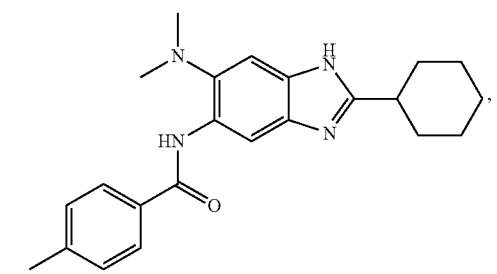 [SMILES: Cc1ccc(C(=O)Nc2cc3nc(C4CCCCC4)[nH]c3cc2N(C)C)cc1]

SB-P17G-A28

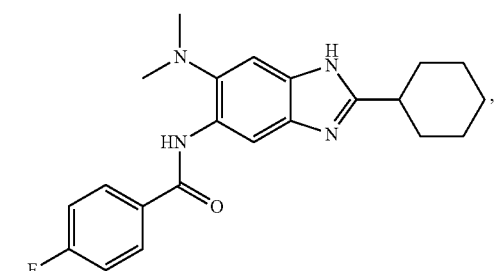

SB-P17G-A24

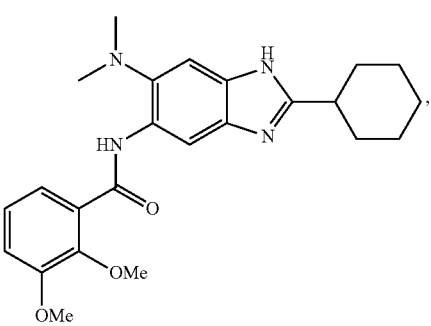 [SMILES: COc1cccc(C(=O)Nc2cc3nc(C4CCCCC4)[nH]c3cc2N(C)C)c1OC]

SB-P17G-A29

-continued

SB-P17G-A32
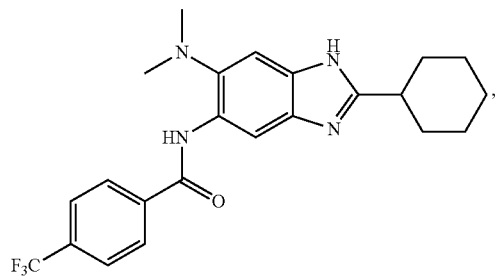

SB-P17G-A33
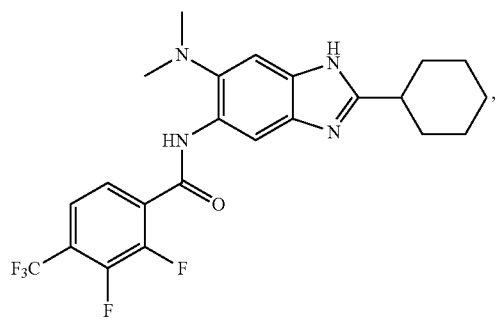 [SMILES: CN(C)c1cc2[nH]c(C3CCCCC3)nc2cc1NC(=O)c1ccc(C(F)(F)F)c(F)c1F]

SB-P17G
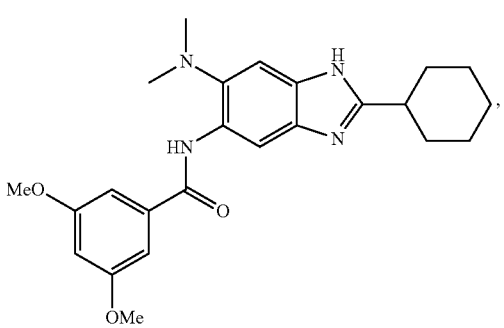

SB-P17G-A42
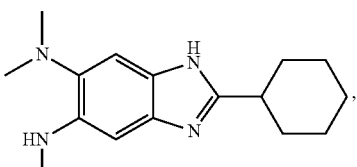

SB-P17G-A40

SB-P17G-A38
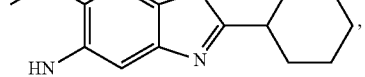

SB-P17G-A34

SB-P17G-A41
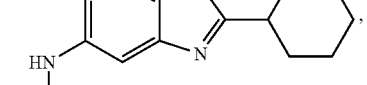

SB-P17G-A10

or a pharmaceutically acceptable salt thereof.

The invention also relates to methods of treating a patient infected by *Mycobacterium tuberculosis* by administering to the patient a benzimidazole of the invention or a pharmaceutically acceptable salt thereof.

DETAILED DESCRIPTION

The invention relates to novel benzimidazole derivatives shown in Table 1 and the benzimidazole derivatives of formula I, or pharmaceutically acceptable salts thereof. These benzimidazole derivatives or pharmaceutically acceptable salts thereof can be used to treat a patient infected by *Mycobacterium tuberculosis*.

TABLE 1
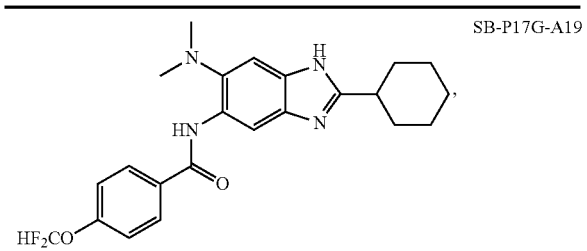
SB-P17G-A19
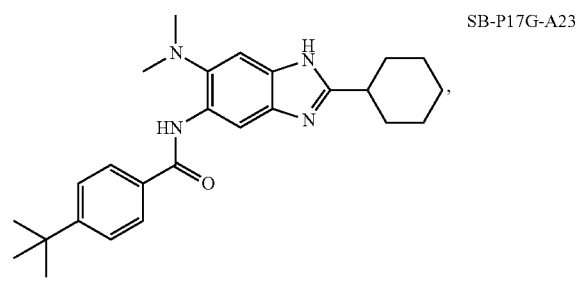
SB-P17G-A23
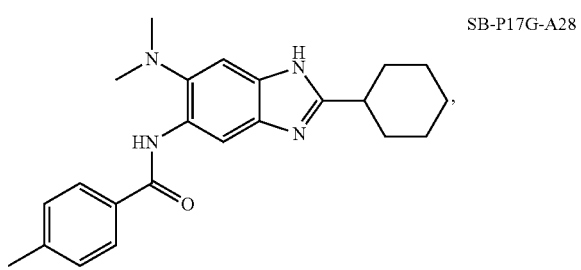
SB-P17G-A28
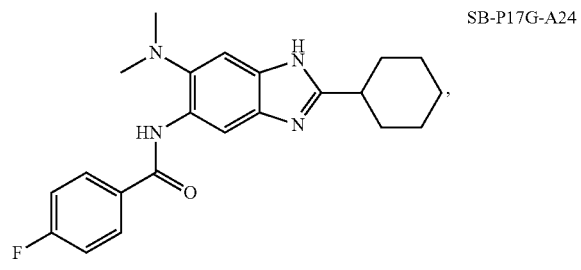
SB-P17G-A24
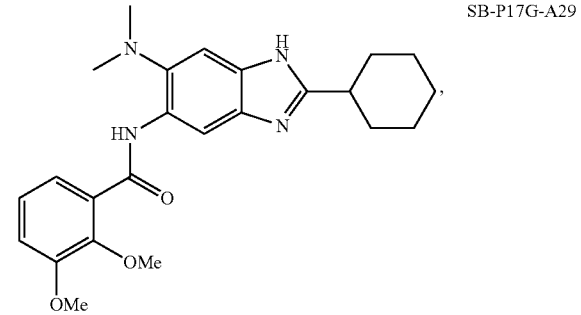
SB-P17G-A29
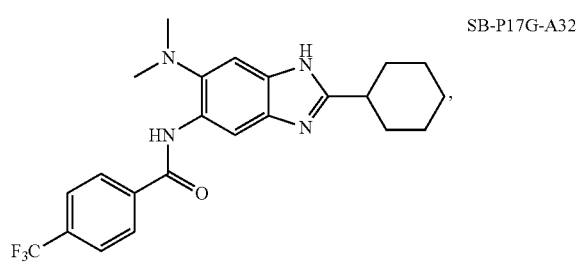
SB-P17G-A32
TABLE 1-continued
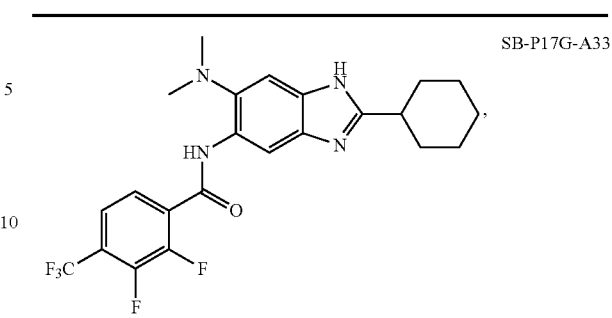
SB-P17G-A33
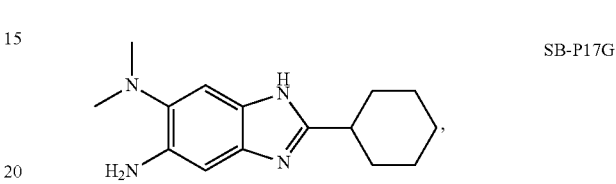
SB-P17G
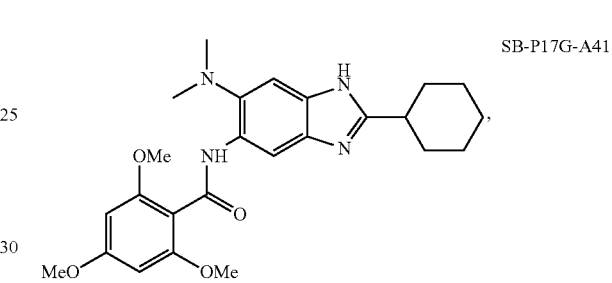
SB-P17G-A41
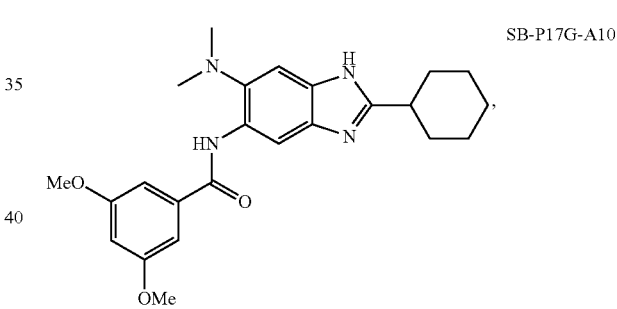
SB-P17G-A10
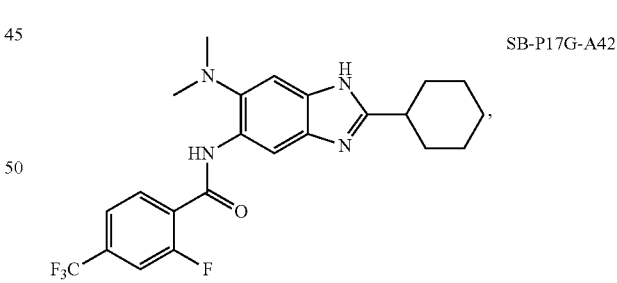
SB-P17G-A42
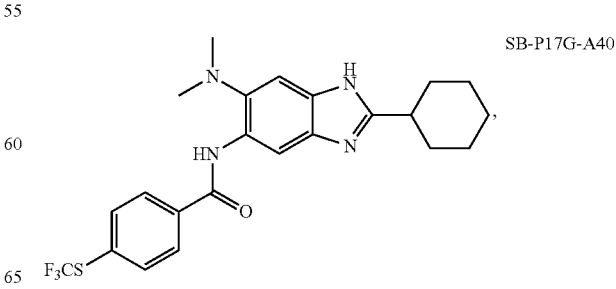
SB-P17G-A40

TABLE 1-continued

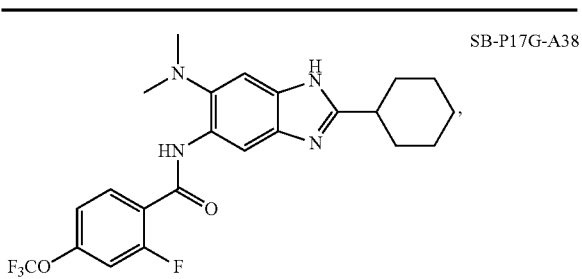

SB-P17G-A38

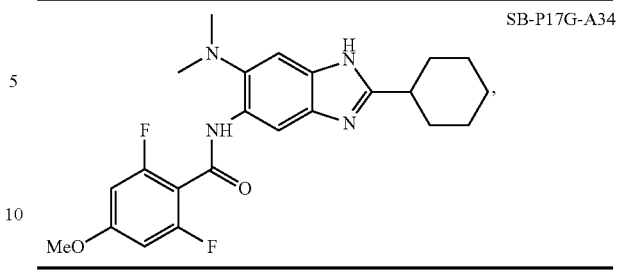

SB-P17G-A34

Synthesis of the Benzimidazole Derivatives

The benzimidazoles of the present invention can be synthesized by methods known in the art. The following scheme represents one approach to the synthesis of the compounds of the invention.

Scheme 1. Synthesis of 2, 5, 6-Trisubstituted Benzimidazoles [a]

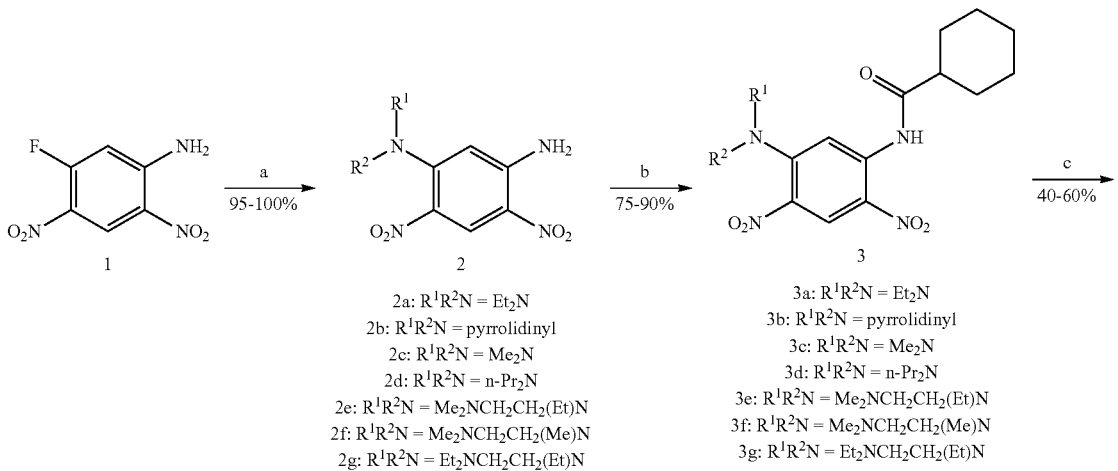

2a: $R^1R^2N$ = $Et_2N$
2b: $R^1R^2N$ = pyrrolidinyl
2c: $R^1R^2N$ = $Me_2N$
2d: $R^1R^2N$ = n-$Pr_2N$
2e: $R^1R^2N$ = $Me_2NCH_2CH_2(Et)N$
2f: $R^1R^2N$ = $Me_2NCH_2CH_2(Me)N$
2g: $R^1R^2N$ = $Et_2NCH_2CH_2(Et)N$ 3a: $R^1R^2N$ = $Et_2N$
3b: $R^1R^2N$ = pyrrolidinyl
3c: $R^1R^2N$ = $Me_2N$
3d: $R^1R^2N$ = n-$Pr_2N$
3e: $R^1R^2N$ = $Me_2NCH_2CH_2(Et)N$
3f: $R^1R^2N$ = $Me_2NCH_2CH_2(Me)N$
3g: $R^1R^2N$ = $Et_2NCH_2CH_2(Et)N$

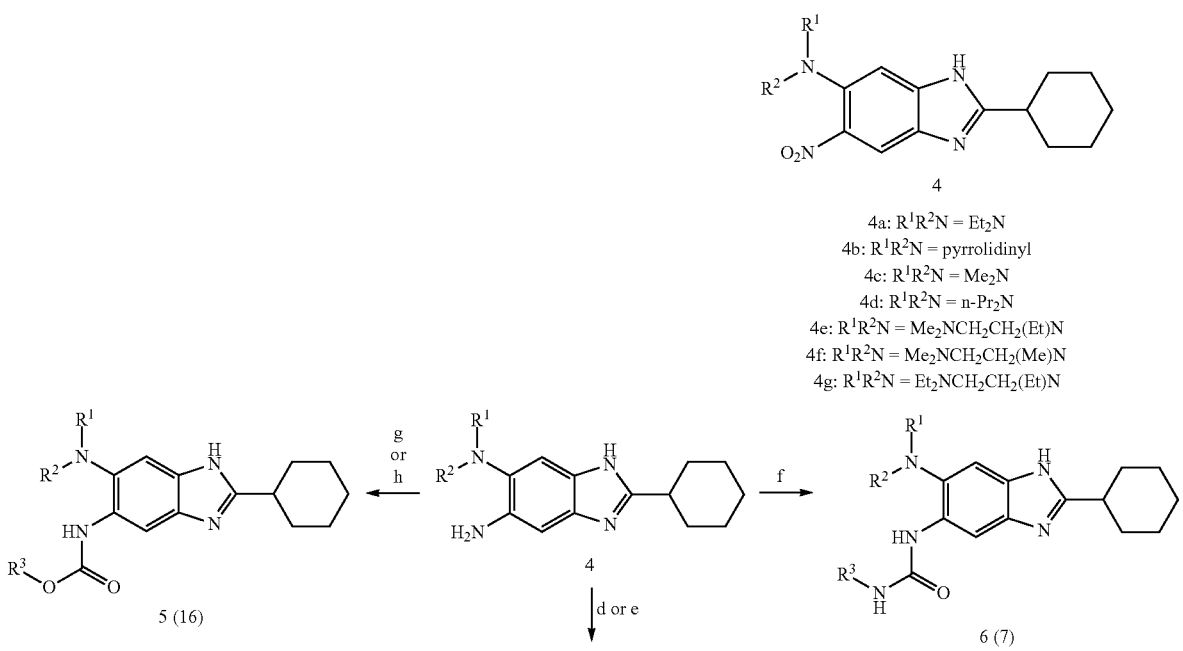

4a: $R^1R^2N$ = $Et_2N$
4b: $R^1R^2N$ = pyrrolidinyl
4c: $R^1R^2N$ = $Me_2N$
4d: $R^1R^2N$ = n-$Pr_2N$
4e: $R^1R^2N$ = $Me_2NCH_2CH_2(Et)N$
4f: $R^1R^2N$ = $Me_2NCH_2CH_2(Me)N$
4g: $R^1R^2N$ = $Et_2NCH_2CH_2(Et)N$ 5 (16)

6 (7)

-continued

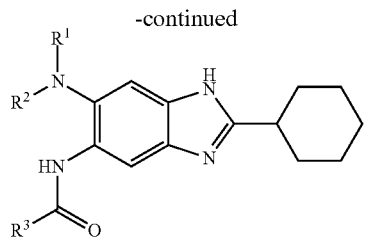

7 (40)

[a]Reagents and conditions: (a) R$^1$R$^2$NH, DIPEA, THF, 2 h, room temperature (RT)/12 h, 50° C.; (b) cyclohexanecarbonyl chloride, pyridine, reflux, overnight; (c) SnCl$_2$•2H$_2$O, 4M HCl, EtOH, reflux, 4 h; (d) R$^3$COCl, Et$_3$N, 0° C.-RT, overnight; (e) R$^3$COOH, EDC•HCl, DMAP, CH$_2$Cl$_2$, reflux, overnight; (f) R$^3$NCO, Et$_3$N, reflux, overnight; (g) (i) 1, 1'-carbonyldiimidazole, CH$_2$Cl$_2$, reflux, 4 h; (ii) R$^3$OH, CH$_2$Cl$_2$, reflux, overnight; (h) R$^3$OSu ester, CH$_2$Cl$_2$, 0° C.-RT, overnight.

Synthesis of compounds for the optimization library of 2,5,6-trisubstituted benzimidazoles (63 compounds in total) is outlined in Scheme 1, which in most part follows the protocol previously published by Dr. Iwao Ojima's laboratory. See Kumar, K.; Awasthi, D.; Lee, S.-Y; Zanardi, I.; Ruzsicska, B.; Knudson, S.; Tonge, P. J.; Slayden, R. A.; Ojima, I., Novel Trisubstituted Benzimidazoles, Targeting Mtb FtsZ, as a New Class of Antitubercular Agents. *J. Med. Chem.* 2011, 54, 374-381. The aromatic nucleophilic substitution of commercially available 2,4-dinitro-5-fluoroaniline with various amines afforded 5-dialkylaminodinitroanilines 2a-g in 94-98% yields. The acylation of 2a-g with cyclohexanecarbonyl chloride gave the corresponding N-acylanilines 3a-g in 75-95% yields. One-pot reduction and the subsequent cyclization in the presence of stannous chloride dihydrate and 4 M hydrochloric acid gave 5-aminobenzimidazoles 4a-g in 65-79% yields. The derivatization of 4a-g was carried out using five different methods depending on the functional group to be introduced, and analytically pure compounds 5, 6 and 7 were obtained in 42-97% yields after chromatographic purification. Compounds 5, 6 and 7 bear a carbamate, urea and amide group, respectively, at the 5 position.

Pharmaceutically Acceptable Salts

The present invention also relates to pharmaceutically acceptable salts of the benzimidazole derivatives. The pharmaceutically acceptable salts include the conventional non-toxic salts of the benzimidazole derivatives as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the benzimidazole derivatives of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Uses of the Benzimidazole Derivatives

The invention also relates to a method of treating a patient infected with *Mycobacterium tuberculosis*. The method comprises administering to the patient the compound of formula (I) or a pharmaceutically acceptable salt thereof.

The method and compounds of the invention may be employed alone, or in combination with other anti-bacterial agents. Other anti-bacterial agents include isoniazid, rifampin, pyrazinamide, rifabutin, streptomycin and ciprofloxacin. The combination of these anti-bacterial agents and the compounds of the invention will provide new agents for the treatment of tuberculosis, including MDR-TB and XDR-TB.

An effective amount of a compound of formula (I) or a pharmaceutically acceptable salt thereof as used herein is any amount effective to treat a patient infected by Mtb. Modes of administration and doses can be determined by those having skill in the art. An effective amount of the compound will vary with the group of patients (age, sex, weight, etc.), the nature and severity of the condition to be treated, the particular compound administered, and its route of administration. Amounts suitable for administration to humans are routinely determined by physicians and clinicians during clinical trials.

The minimum dose of the compound is the lowest dose at which efficacy is observed. For example, the minimum dose of the compound may be about 0.1 mg/kg/day, about 1 mg/kg/day, or about 3 mg/kg/day.

The maximum dose of the compound is the highest dose at which efficacy is observed in a patient, and side effects are tolerable. For example, the maximum dose of the compound may be about 10 mg/kg/day, about 9 mg/kg/day, or about 8 mg/kg/day. In another embodiment, the maximum dose of the compound may be up to about 50 mg/kg/day.

A benzimidazole derivative useful in the methods of the present invention may be administered by any method known in the art. Some examples of suitable modes of administration include oral and systemic administration. Systemic administration can be enteral or parenteral. Liquid or solid (e.g., tablets, gelatin capsules) formulations can be employed.

Parenteral administration of the benzimidazole derivative include, for example intraperitoneal, intravenous, intramuscular, and subcutaneous injections. For instance, a chemical compound may be administered to a patient by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a chemical compound can be accomplished by a nebulizer or liquid mist.

The chemical compound can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The chemical compound can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the chemical compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v). Other preferred surfactants include Solutol H-15 and Cremophore EL.

The salt or buffering agent may be any salt or buffering agent, such as for example sodium chloride, or sodium/potassium phosphate, respectively. Preferably, the buffering agent maintains the pH of the chemical compound formulation in the range of about 5.5 to about 7.5. The salt and/or buffering agent is also useful to maintain the osmolality at a level suitable for administration to a patient. Preferably the salt or buffering agent is present at a roughly isotonic concentration of about 150 mM to about 300 mM.

The chemical compound can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as, for example a morphine derivative; or an isotonic agent etc. As a further precaution against oxidation or other spoilage, the composition may be stored under nitrogen gas in vials sealed with impermeable stoppers.

Further information regarding the synthesis, characterization and antibacterial activity of the compounds can be found in Awasthi, et al. "SAR Studies on Trisubstituted Benzimidazoles as Inhibitors of MTb FtsZ for the Development of Novel Antitubercular Agents" J. Med. Chem., 2013, 56 (23), pp 9756-9770, the entirety of which is hereby incorporated by reference.

EXAMPLES

Examples have been set forth below for the purposes of illustration and to describe the best mode of the invention at the present time. The scope of the invention is not to be in any way limited by the examples set forth herein.

Example I. Synthesis of Compounds and Characterization

5-N,N-Dimethylamino-2,4-dinitroaniline

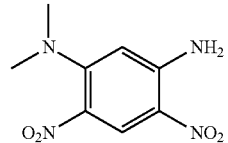 [SMILES: CN(C)c1cc(N)c([N+](=O)[O-])cc1[N+](=O)[O-]]

To a solution of 2,4-dinitro-5-fluoroaniline (9.92 g, 49 mmol) and DIPEA (54 mmol) in tetrahydrofuran (150 mL) was added a solution of dimethylamine (2 M in THF, 54 mmol) in tetrahydrofuran (10 mL), drop wise and the mixture was stirred at room temperature for 4 h. After completion of reaction, the reaction mixture was diluted with dichloromethane, transferred to a separatory funnel and washed with water (30 mL×3), dried over anhydrous magnesium sulfate, filtered, rotary evaporated and dried under vacuum to afford 1.1 as a yellow solid. (10.82 g, 97.1% yield): mp 162-165° C.; $^1$H NMR (400 MHz, CDCl$_3$) δ 2.94 (s, 6H), 6.01 (s, 1H), 6.41 (s, 2H), 8.80 (s, 1H).

1-Cyclohexanecarboxamido-5-N,N-dimethylamino-2,4-dinitrobenzene

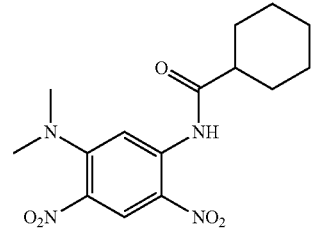 [SMILES: CN(C)c1cc(NC(=O)C2CCCCC2)c([N+](=O)[O-])cc1[N+](=O)[O-]]

A solution of 5-N,N-dimethylamino-2,4-dinitro aniline (2.22 g, 9.8 mmol.) and cyclohexanecarbonyl chloride (1.5 mL, 10.78 mmol) in pyridine (12 mL) was refluxed overnight. The reaction mixture concentrated on a rotary evaporator and the crude reside was washed with methanol to obtain the product 1-cyclohexanecarboxamido-5-(N,N-dimethylamino)-2,4-dinitrobenzene as yellow solid (2.96 g, 90% yield); mp 148-149° C.; $^1$H NMR (300 MHz, CDCl$_3$) δ 1.2-1.3 (m, 4H), 1.73 (m, 1H), 1.86 (m, 2H), 2.03 (m, 2H), 2.38 (m, 1H), 3.06 (s, 6H), 8.60 (s, 1H), 8.85 (s, 1H), 11.00 (s, 1H); $^{13}$C NMR (101 MHz, CDCl$_3$) δ 25.5, 25.6, 29.4, 42.5, 47.3, 106.1, 125.0, 127.4, 131.3, 138.7, 150.1, 175.9.

2-Cyclohexyl-5-(4-difluoromethoxybenzamido)-6-N,N-dimethylamino1H-benzo[d]imidazole

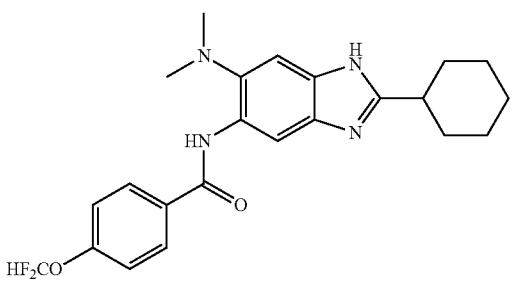

SB-P17G-A19
MIC$_{99}$ 0.31 µg/mL
MIC$_{50}$ 0.28 µg/mL

White solid (65% yield); mp 183-185° C.; $^1$H NMR (400 MHz, CDCl$_3$) δ 1.02-1.33 (m, 5H), 1.51-1.79 (m, 6H), 2.00 (d, J=13.55 Hz, 2H), 2.72 (s, 7H), 6.61 (d, J=73.53 Hz, 1H), 7.25-7.31 (m, 2H), 7.59 (s, 1H), 7.97 (d, J=9.03 Hz, 2H), 8.82 (s, 1H), 9.87 (s, 1H); $^{13}$C NMR (126 MHz, CDCl$_3$) δ 14.3, 25.9, 26.1, 31.8, 32.0, 34.9, 38.7, 46.1, 101.8, 110.9, 113.5, 115.6, 117.7, 119.7, 128.9, 129.1, 132.7, 139.5, 153.8, 160.1, 164.4; HPLC (1): t=12.8 min, purity >99%.

2-Cyclohexyl-6-N,N-dimethylamino-5-(4-methylbenzamido)-1H-benzo[d]imidazole

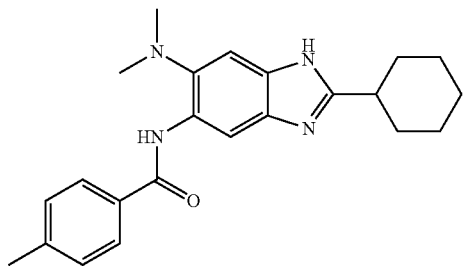

SB-P17G-A28
MIC$_{99}$ 0.31 µg/mL
MIC$_{50}$ 0.22 µg/mL

White solid (76% yield); mp 179-180° C.; $^1$H NMR (500 MHz, CDCl$_3$) δ 1.05-1.27 (m, 3H), 1.50-1.77 (m, 5H), 1.99 (d, J=12.51 Hz, 2H), 2.46 (s, 3H), 2.66-2.78 (m, 7H), 7.35 (d, J=8.24 Hz, 2H), 7.61 (s, 1H), 7.87 (d, J=8.24 Hz, 2H), 8.89 (s, 1H), 9.90 (s, 1H), 10.65 (br. s, 1H); $^{13}$C NMR (126 MHz, CDCl$_3$) δ 21.7, 25.9, 26.2, 32.0, 38.6, 46.1, 101.7, 110.9, 127.2, 129.2, 129.8, 131.3, 133.0, 139.4, 139.8, 142.5, 159.9, 165.7; HPLC (1): t=10.6 min, purity >99%.

5-(4-tert-Butylbenzamido)-2-cyclohexyl-6-N,N-dimethylamino-1H-benzo[d]imidazole

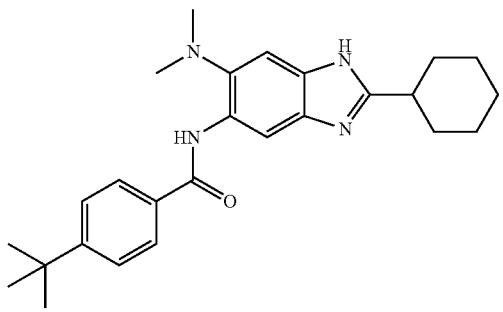

SB-P17G-A23
MIC$_{99}$ 1.56 µg/mL
MIC$_{50}$ 0.75 µg/mL

White solid (74% yield); mp 222-223° C.; $^1$H NMR (500 MHz, CDCl$_3$) δ 0.96-1.20 (m, 4H), 1.39 (s, 9H), 1.49-1.72 (m, 5H), 1.96 (d, J=12.21 Hz, 2H), 2.74 (s, 7H), 7.58 (d, J=8.24 Hz, 3H), 7.93 (d, J=8.54 Hz, 2H), 8.97 (s, 1H), 9.98 (s, 1H), 11.00 (s, 1H); $^{13}$C NMR (126 MHz, CDCl$_3$) δ 25.8, 26.1, 31.4, 32.0, 35.2, 38.6, 46.2, 101.7, 110.9, 126.2, 127.1, 129.2, 133.0, 139.3, 139.8, 155.5, 160.1, 165.8; HPLC (1): t=9.0 min, purity >99%.

2-Cyclohexyl-5-(4-fluorobenzamido)-6-N,N-dimethylamino-1H-benzo[d]imidazole

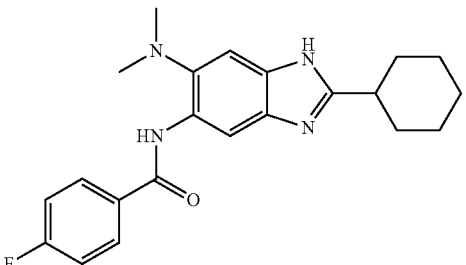

SB-P17G-A24
MIC$_{99}$ 0.63 µg/mL
MIC$_{50}$ 0.49 µg/mL

White solid (70% yield); mp 196-197° C.; $^1$H NMR (500 MHz, Methanol-d$_4$) δ 2.00-2.26 (m, 3H), 2.34-2.45 (m, 2H), 2.46-2.55 (m, 1H), 2.60 (dt, J=12.97, 3.28 Hz, 2H), 2.81 (d, J=13.12 Hz, 2H), 3.48 (s, 6H), 3.58-3.67 (m, 1H), 8.20 (t, J=8.85 Hz, 2H), 8.82 (dd, J=8.85, 5.49 Hz, 2H), 9.07 (br. s, 1H), 10.50 (br. s, 1H), 12.80 (s, 1H); $^{13}$C NMR (126 MHz, Methanol-d$_4$) δ 35.1, 35.2, 40.9, 47.3, 54.9, 111.6, 112.1, 119.5, 121.1, 125.3, 125.5, 136.7, 137.5, 139.2, 139.3, 140.3, 141.1, 141.1, 149.3, 150.7, 168.8, 172.7, 174.7; HPLC (1): t=11.4 min, purity >99%.

Same procedure was followed for the synthesis of SB-P17G-A29, SB-P17G-A32, and SB-P17G-A33.

2-Cyclohexyl-5-(2,3-dimethoxybenzamido)-6-N,N-dimethylamino-1H-benzo[d]imidazole

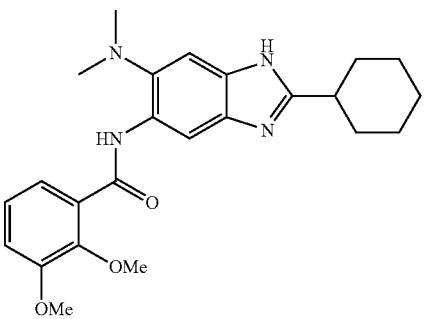

SB-P17G-A29
MIC$_{99}$ 0.63 µg/mL
MIC$_{50}$ n.d

White solid (84% yield); mp 173-174° C.; $^1$H NMR (500 MHz, CDCl$_3$) δ 0.99-1.21 (m, 3H), 1.44-1.61 (m, 2H), 1.66 (d, J=13.12 Hz, 2H), 1.96 (d, J=11.90 Hz, 2H), 2.62-2.81 (m, 7H), 3.96 (s, 6H), 6.99 (d, J=8.54 Hz, 1H), 7.50 (dd, J=8.24, 1.83 Hz, 1H), 7.53-7.63 (m, 2H), 8.85 (s, 1H), 9.85 (s, 1H); $^{13}$C NMR (126 MHz, CDCl$_3$) δ 25.8, 26.1, 31.9, 38.7, 46.0, 56.2, 56.3, 102.2, 110.1, 110.8, 110.9, 119.7, 128.2, 129.1, 131.9, 138.7, 139.4, 149.4, 152.2, 159.9, 165.2.

2-Cyclohexyl-5-(4-trifluoromethylbenzamido)-6-N,N-dimethylamino-1H-benzo[d]imidazole

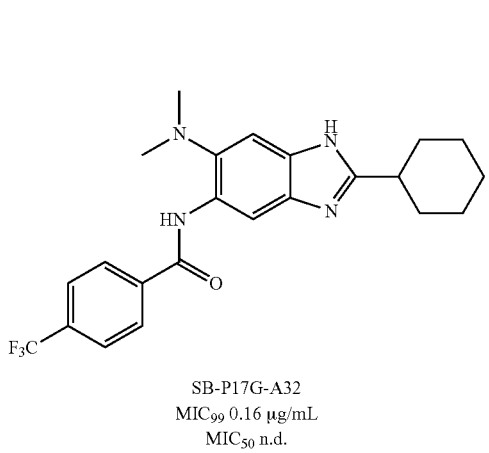

SB-P17G-A32
MIC$_{99}$ 0.16 μg/mL
MIC$_{50}$ n.d.

Yellow solid (79% yield); $^1$H NMR (400 MHz, CDCl$_3$) δ 1.09-1.34 (m, 3H), 1.51-1.83 (m, 5H), 2.04 (d, J=11.80 Hz, 2H), 2.66-2.87 (m, 7H), 7.61 (br. s., 1H), 7.82 (d, J=8.03 Hz, 2H), 8.07 (d, J=8.03 Hz, 2H), 8.83 (s, 1H), 9.97 (br. s., 1H); $^{13}$C NMR (101 MHz, CDCl$_3$) δ 25.9, 26.1, 32.0, 38.7, 46.2, 102.1, 110.8, 122.5, 125.2, 126.2, 126.2, 126.2, 127.6, 128.9, 133.5, 133.8, 139.1, 139.6, 160.1, 164.2.

2-Cyclohexyl-5-(2,3-difluoro-4-trifluoromethylbenzamido)-6-N,N-dimethylamino-1H-benzo[d]imidazole

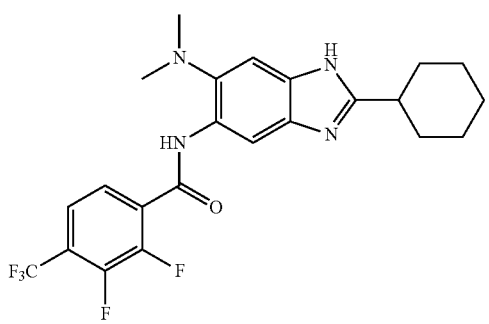

SB-P17G-A33
MIC$_{99}$ 0.62 μg/mL
MIC$_{50}$ 0.38 μg/mL

Yellow solid (84% yield); $^1$H NMR (500 MHz, CDCl$_3$) δ 1.12-1.36 (m, 3H), 1.64 (d, J=10.68 Hz, 1H), 1.70-1.94 (m, 4H), 2.18 (d, J=11.90 Hz, 2H), 2.64 (br. s., 6H), 3.04-3.27 (m, 1H), 7.51 (d, J=5.80 Hz, 1H), 7.64 (br. s., 1H), 7.92 (br. d, J=5.80 Hz, 1H), 8.84 (br. s., 1H), 10.13 (br. s., 1H), 10.40 (br. s., 1H); $^{13}$C NMR (126 MHz, CDCl$_3$) δ 25.5, 25.9, 31.6, 37.9, 45.6, 104.6, 107.7, 118.4, 120.6, 122.1, 122.5, 122.6, 122.7, 122.7, 122.8, 123.0, 123.0, 123.1, 123.1, 123.3, 123.3, 123.4, 124.9, 124.9, 126.3, 127.5, 127.6, 130.6, 131.1, 132.5, 141.5, 147.4, 147.5, 147.9, 148.0, 149.5, 149.6, 149.9, 150.1, 158.6, 159.1.

5-Amino-2-cyclohexyl-6-N,N-dimethylamino-1H-benzo[d]imidazole

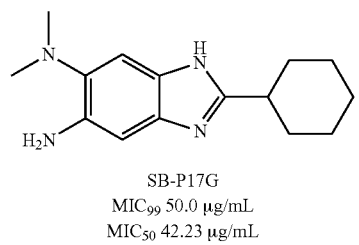

SB-P17G
MIC$_{99}$ 50.0 μg/mL
MIC$_{50}$ 42.23 μg/mL

Light brown solid (69% yield); mp 135-137° C.; $^1$H NMR (300 MHz, CDCl3) δ 1.14-1.46 (m, 3H), 1.54-1.86 (m, 5H), 1.99-2.17 (m, 2H), 2.64 (s, 6H), 2.73-2.87 (m, 1H), 6.81 (s, 5H), 7.26 (s, 1H); $^{13}$C NMR (101 MHz, CDCl$_3$) δ 26.0, 26.2, 32.2, 38.8, 44.8, 98.9, 106.7, 133.1, 134.5, 138.0, 138.3, 158.2.

The procedure used for synthesis of SB-P17G was followed to synthesis SB-P17G-A41, SB-P17G-A10, SB-P17G-A42, SB-P17G-A40, SB-P17G-A38.

2-Cyclohexyl-5-(2,4,6-trimethoxybenzamido)-6-N,N-dimethylamino-1H-benzo[d]imidazole

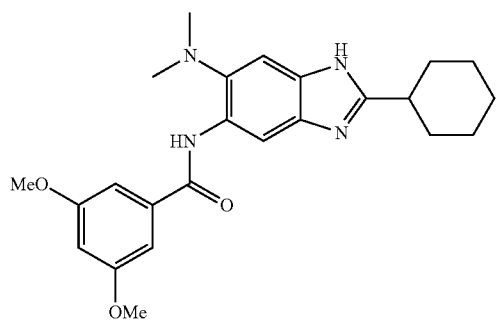

SB-P17G-A41
MIC$_{99}$ < 0.78 μg/mL

White solid; $^1$H NMR (300 MHz, ACETONE-d$_6$) δ 1.21-1.49 (m, 3H), 1.54-1.88 (m, 6H), 2.66 (s, 6H), 3.77-3.96 (m, 9H), 6.33 (s, 2H), 7.30-7.55 (m, 1H), 8.67-8.88 (m, 1H), 9.02 (br. s, 1H).

2-Cyclohexyl-5-(3,5-methoxybenzamido)-6-N,N-dimethylamino-1H-benzo[d]imidazole SB-P17G-A10
MIC$_{99}$ 0.625 μg/mL
IC$_{50}$ 0.479 μg/mL White solid (82% yield); $^1$H NMR (500 MHz, CDCl$_3$) δ 1.00-1.20 (m, 3H), 1.49-1.71 (m, 5H), 1.95 (d, J=11.60 Hz, 2H), 2.65-2.76 (m, 7H), 3.86 (s, 6H), 6.65 (t, J=2.14 Hz, 1H), 7.08 (d, J=2.14 Hz, 2H), 7.56 (br. s., 1H), 8.90 (s, 1H), 9.86 (br. s., 1H); $^{13}$C NMR (126 MHz, CDCl$_3$) δ 25.8, 26.1, 32.0, 38.7, 46.0, 55.7, 101.9, 103.5, 105.2, 110.7, 128.8, 131.5, 138.0, 139.4, 139.7, 160.2, 161.3, 165.6.

2-Cyclohexyl-5-(2-fluoro-4-trifluoromethylbenzamido)-6-N,N-dimethylamino-1H-benzo[d]imidazole

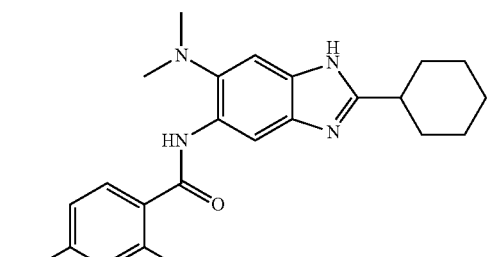

SB-P17G-A42
MIC$_{99}$ 0.156 μg/mL
MIC$_{50}$ 0.143 μg/mL

Yellow solid (58% yield); $^1$H NMR (300 MHz, CDCl$_3$) δ 1.04-1.39 (m, 3H), 1.49-1.88 (m, 5H), 1.95-2.14 (m, 2H), 2.57-2.91 (m, 7H), 7.41-7.79 (m, 3H), 8.33 (t, J=7.73 Hz, 3H), 8.86 (s, 3H), 10.25-10.76 (m, J=8.75 Hz, 2H).

2-Cyclohexyl-5-(4-trifluoromethylthiobenzamido)-6-N,N-dimethylamino-1H-benzo[d]imidazole

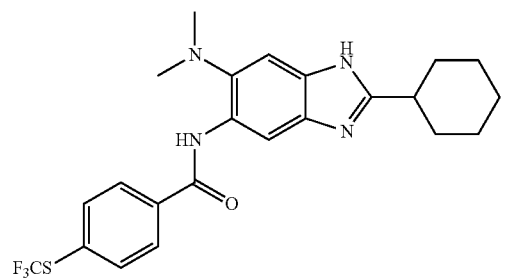

SB-P17G-A40
MIC$_{99}$ 0.31 μg/mL
IC$_{50}$ 0.24 μg/mL

Brown solid (56% yield); $^1$H NMR (300 MHz, CDCl$_3$) δ 0.98-1.29 (m, 3H), 1.47-1.83 (m, 5H), 2.01 (d, J=11.73 Hz, 2H), 2.74 (s, 7H), 7.62 (br. s., 1H), 7.85 (d, J=7.82 Hz, 2H), 8.02 (d, J=8.20 Hz, 2H), 8.87 (s, 1H), 10.04 (br. s., 3H), 11.00 (br. s, 1H).

2-Cyclohexyl-5-(2-fluoro-4-trifluoromethoxybenzamido)-6-N,N-dimethylamino-1H-benzo[d]imidazole

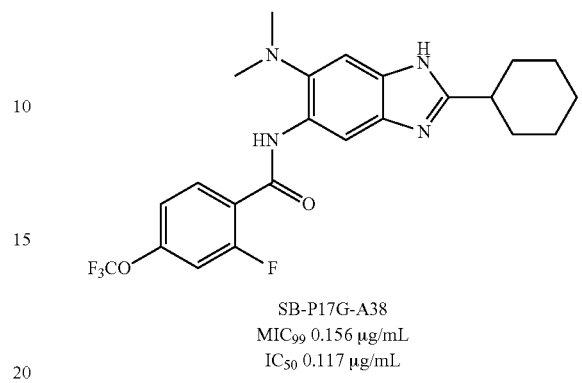

SB-P17G-A38
MIC$_{99}$ 0.156 μg/mL
IC$_{50}$ 0.117 μg/mL

Yellow solid (82% yield); $^1$H NMR (300 MHz, CDCl$_3$) δ 1.11-1.40 (m, 3H), 1.51-1.88 (m, 5H), 2.07 (d, J=11.92 Hz, 2H), 2.63-2.88 (m, 7H), 7.06-7.25 (m, 2H), 7.62 (br. s., 1H), 8.28 (t, J=8.75 Hz, 1H), 8.82 (br. s., 1H), 9.87 (br. s., 1H), 10.37 (br. s., 3H).

2-Cyclohexyl-5-(2,6-difluoro-4-methoxybenzamido)-6-N,N-dimethylamino-1H-benzo[d]imidazole

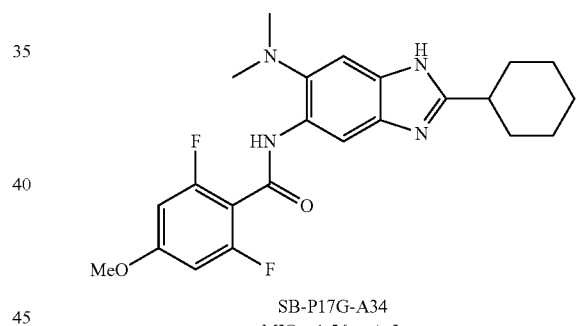

SB-P17G-A34
MIC$_{99}$ 1.56 μg/mL
MIC$_{50}$ 1.06 μg/mL

Light brown solid (53% yield); $^1$H NMR (500 MHz, CDCl3) δ 1.12-1.26 (m, 3H), 1.50-1.75 (m, 5H), 2.01 (d, J=11.90 Hz, 2H), 2.60-2.80 (m, 7H), 3.86 (s, 3H), 6.59 (d, J=9.77 Hz, 2H), 7.58 (br. s., 1H), 8.90 (s, 1H), 9.62 (br. s, 1H); 13C NMR (126 MHz, CDCl3) δ 25.9, 26.3, 31.9, 38.7, 46.1, 56.3, 98.8, 99.0, 102.6, 107.6, 107.8, 107.9, 110.5, 128.8, 131.7, 139.3, 139.8, 158.5, 160.2, 160.3, 160.4, 162.3, 162.4, 162.5, 162.6, 162.7; HRMS (FAB) m/z calcd for C23H26F2N4O2H+: 429.2097, Found: 429.2098 (Δ=0.2 ppm).

Example II. Screening of Compounds

MIC values were determined using the microplate dilution method reported by R. A. Slayden et al, "The role of KasA and KasB in the biosynthesis of meromycolic acids and isoniazid resistance in Mycobacterium tuberculosis", Tuberculosis (Edinburgh, 2002) Vol. 82, pages 149-60. Bacteria were cultivated in liquid medium to an optical density of ~0.4 at 600 nm. The bacterial cultures were then prepared for testing by diluting 1:100 in liquid medium. A total of 50 μL of each culture was added to each well of a 96-well optical plate. Analogs were prepared at 60 μM in 100% DMSO. Compound stock solutions were diluted 1:2 in liquid medium and then distributed in the plate as 2-fold serial dilutions to achieve a concentration range of 200-0.2 mg/mL in a total final volume of 100 μL. The plates were incubated at 37° C. and evaluated for the presence of bacterial growth or non-growth by optical density using an inverted plate reading method. The MIC50 was determined to be the lowest concentration of compound that inhibited 50% bacterial growth. The MIC99 was determined to be the lowest concentration of compound that inhibited 99% bacterial growth. The results are shown below.

Accurate MIC Values

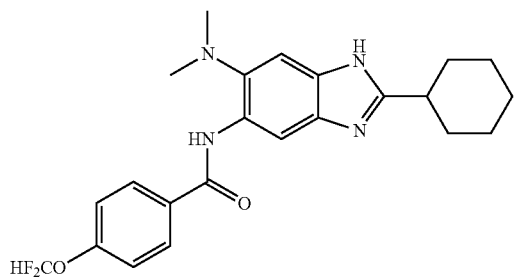

SB-P17G-A19
$MIC_{99}$ 0.31 μg/mL
$MIC_{50}$ 0.28 μg/mL

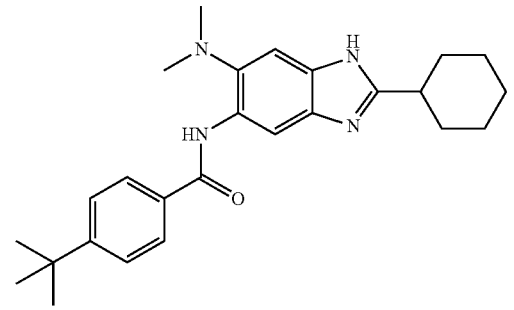

SB-P17G-A23
$MIC_{99}$ 1.56 μg/mL
$MIC_{50}$ 0.75 μg/mL

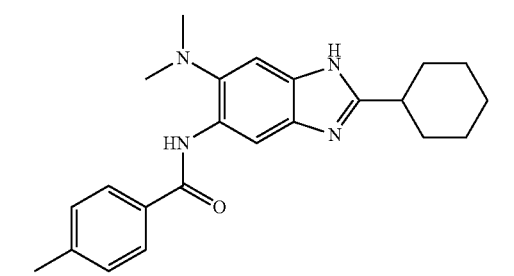

SB-P17G-A28
$MIC_{99}$ 0.31 μg/mL
$MIC_{50}$ 0.22 μg/mL

-continued

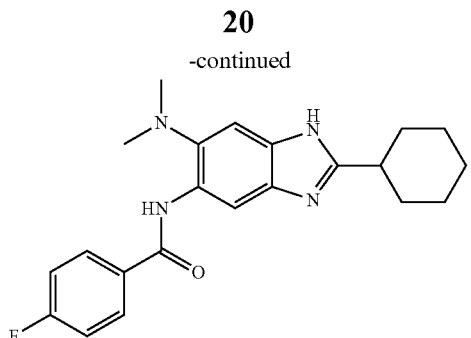

SB-P17G-A24
$MIC_{99}$ 0.63 μg/mL
$MIC_{50}$ 0.49 μg/mL

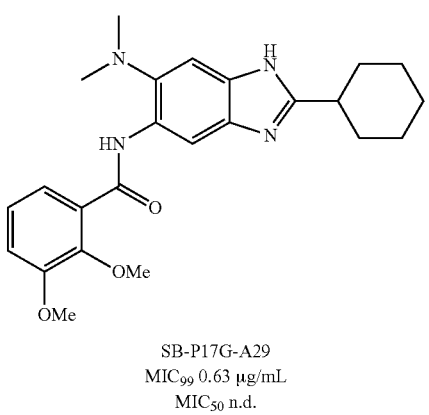 [SMILES: COc1cccc(C(=O)Nc2cc3nc(C4CCCCC4)[nH]c3cc2N(C)C)c1OC]

SB-P17G-A29
$MIC_{99}$ 0.63 μg/mL
$MIC_{50}$ n.d.

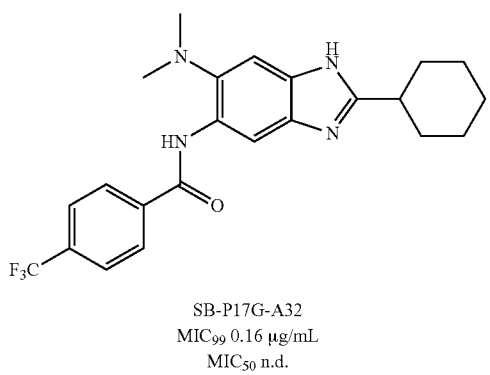 [SMILES: CN(C)c1cc2[nH]c(C3CCCCC3)nc2cc1NC(=O)c1ccc(C(F)(F)F)cc1]

SB-P17G-A32
$MIC_{99}$ 0.16 μg/mL
$MIC_{50}$ n.d.

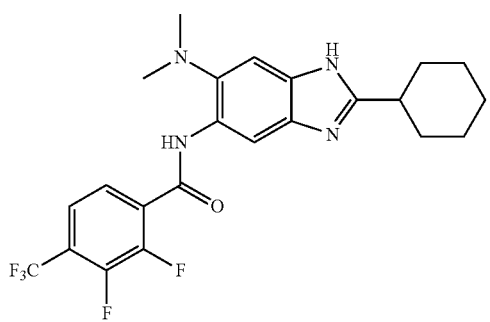

SB-P17G-A33
$MIC_{99}$ 0.62 μg/mL
$MIC_{50}$ 0.38 μg/mL

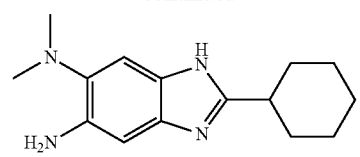
SB-P17G
MIC$_{99}$ 50.0 μg/mL
MIC$_{50}$ 42.23 μg/mL
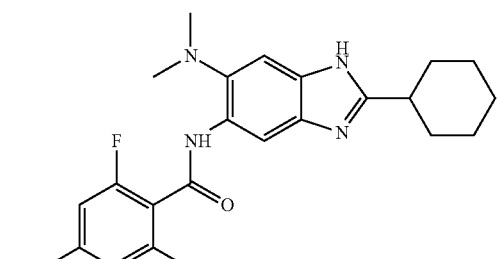
SB-P17G-A34
MIC$_{99}$ 1.56 μg/mL
MIC$_{50}$ 1.06 μg/mL
We claim:
1. A compound having the formula:
SB-P17G-A19
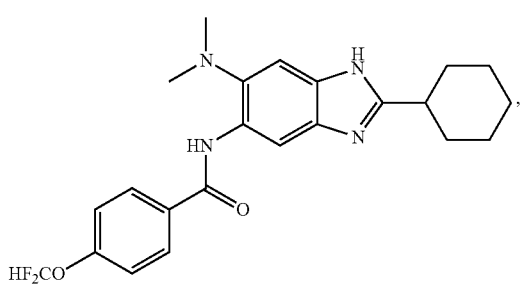
SB-P17G-A32
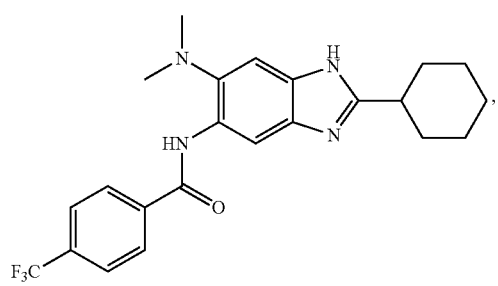
SB-P17G-A33
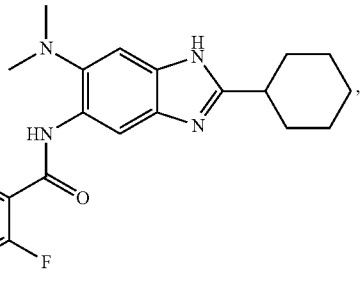
SB-P17G-A42
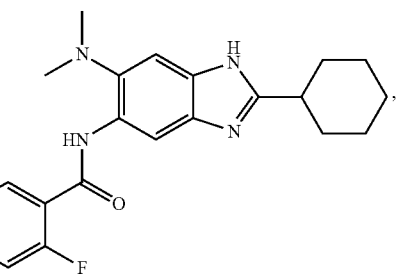
SB-P17G-A38
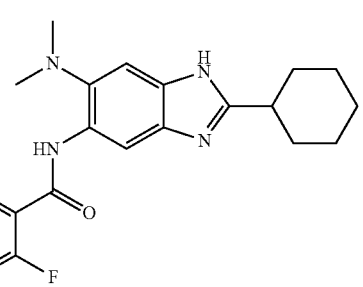
SB-P17G-A34
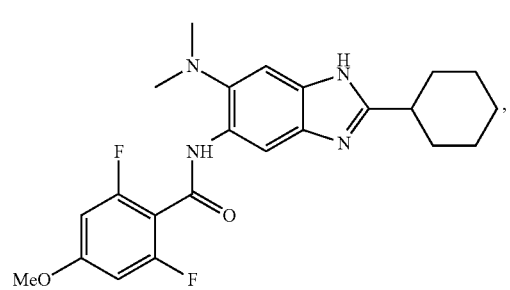
or a pharmaceutically acceptable salt thereof.
2. A method of treating a patient infected with *Mycobacterium tuberculosis*, the method comprising administering to the patient a compound having the formula:

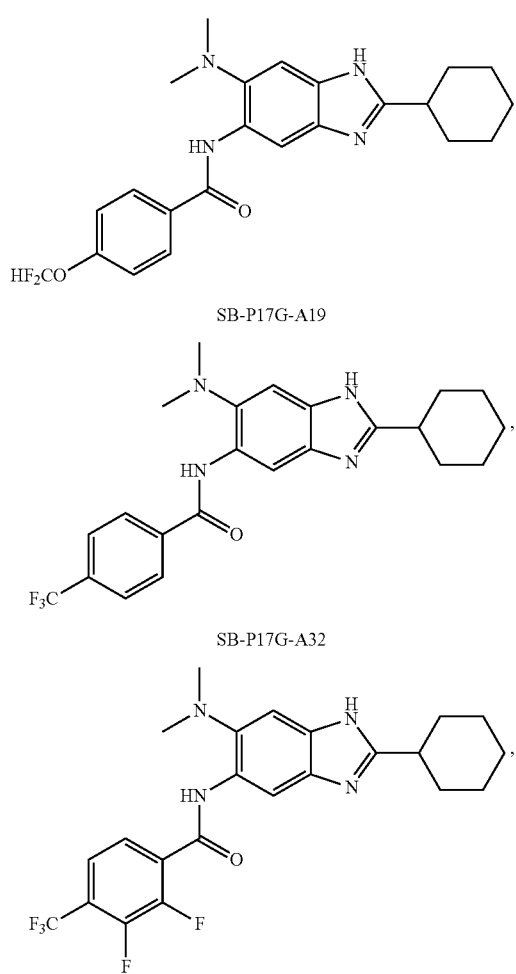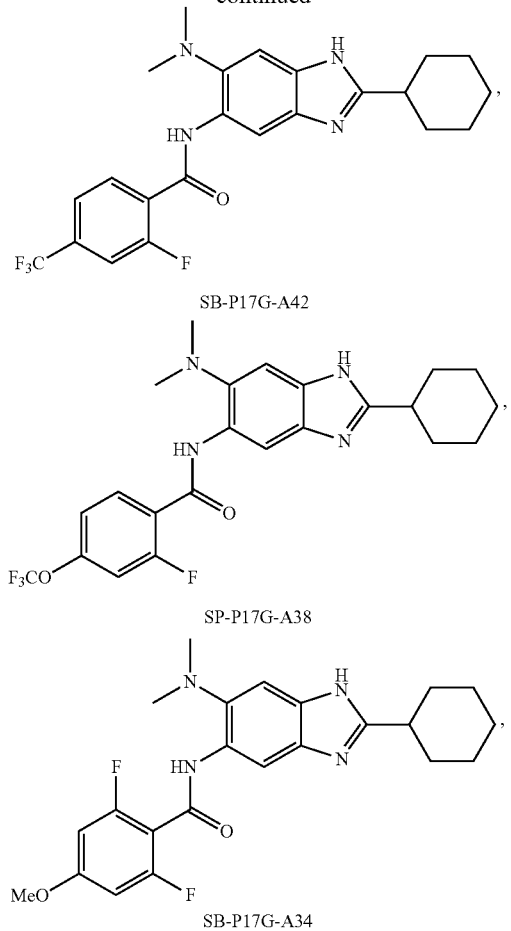
or a pharmaceutically acceptable salt thereof.
* * * * *